(12) United States Patent
Porter et al.

(10) Patent No.: US 10,426,700 B2
(45) Date of Patent: Oct. 1, 2019

(54) SYRINGE ACCESSORY FOR TRANSFER OF AIR SENSITIVE MATERIALS

(71) Applicant: International Business Machines Corporation, Armonk, NY (US)

(72) Inventors: Jacob T. Porter, Highland, NY (US); Joseph Kuczynski, North Port, FL (US); Jason T. Wertz, Pleasant Valley, NY (US); Brandon M. Kobilka, Tucson, AZ (US)

(73) Assignee: International Business Machines Corporation, Armonk, NY (US)

( * ) Notice: Subject to any disclaimer, the term of this patent is extended or adjusted under 35 U.S.C. 154(b) by 112 days.

(21) Appl. No.: 15/824,634

(22) Filed: Nov. 28, 2017

(65) Prior Publication Data

US 2019/0159969 A1    May 30, 2019

(51) Int. Cl.
*A61J 1/20* (2006.01)
*A61M 5/168* (2006.01)
*A61M 5/32* (2006.01)
*A61J 1/14* (2006.01)
*A61M 5/31* (2006.01)

(52) U.S. Cl.
CPC ........... *A61J 1/2003* (2015.05); *A61J 1/1406* (2013.01); *A61M 5/16822* (2013.01); *A61M 5/32* (2013.01); *A61J 1/1443* (2013.01); *A61J 1/2096* (2013.01); *A61M 2005/3118* (2013.01)

(58) Field of Classification Search
CPC ...... A61J 1/2003; A61J 1/1406; A61J 1/1443; A61J 1/2096; A61M 5/16822; A61M 5/32; A61M 2005/3118
See application file for complete search history.

(56) References Cited

U.S. PATENT DOCUMENTS

| 2,862,307 A | 12/1958 | Bloomer et al. |
| 4,813,940 A | 3/1989 | Parry |
| 4,822,340 A * | 4/1989 | Kamstra ............. A61M 5/2066 604/135 |

(Continued)

FOREIGN PATENT DOCUMENTS

GB        2446778 A     8/2008

OTHER PUBLICATIONS

International Search Report and Written Opinion for Application PCT/IB2018/058808, dated Feb. 27, 2019, 10 pgs.

(Continued)

*Primary Examiner* — Jason K Niesz
(74) *Attorney, Agent, or Firm* — Kelsey M. Skodje (57) ABSTRACT

An apparatus, method, and article of manufacture for transferring fluid contained in a syringe. The apparatus includes an airlock component having a cylindrical body with a first end, a second end, and a hollow tube disposed between the first end and the second end. An annular opening is located at the first end of the cylindrical body. The hollow tube includes a gas inlet aperture and a gas outlet aperture. The hollow tube also includes an inwardly-facing airtight material coupled to the interior surface of the hollow tube, and a septum coupled to the second end of the cylindrical body. The method includes transferring fluid from one container to a second container using the apparatus. The article of manufacture includes the apparatus, a syringe, and a needle.

20 Claims, 5 Drawing Sheets

(56) References Cited

U.S. PATENT DOCUMENTS

| | | | |
|---|---|---|---|
| 4,826,665 | A | 5/1989 | Fannin et al. |
| 4,857,053 | A | 8/1989 | Dalton |
| 5,216,175 | A | 6/1993 | Avery et al. |
| 9,358,182 | B2 | 6/2016 | Garfield et al. |
| 2010/0106138 | A1* | 4/2010 | Chavarria ........ A61B 17/00491 604/518 |
| 2013/0134350 | A1 | 5/2013 | Rieke |
| 2014/0018731 | A1* | 1/2014 | Menassa ................ A61M 5/30 604/68 |
| 2016/0206512 | A1 | 7/2016 | Chhikara et al. |
| 2017/0143587 | A1 | 5/2017 | Ivosevic et al. |

OTHER PUBLICATIONS

"Proceudres for Safe Use of Pyrophoric Liquid Reagents," UCLA Chemistry & Biochemistry, 2009, pp. 1-5, UCLA. http://www.chemistry.ucla.edu/sites/default/files/safety/sop/SOP_Pyrophoric_Liquid_Reagents.pdf.

Alnajjar et al., "Handling Pyrophoric Reagents," PNNL-18668, Aug. 2009, 24 pages, Pacific Northwest National Laboratory for the US Department of Energy. https://www.pnl.gov/main/publications/external/technical_reports/PNNL-18668.pdf.

"Pyrophoric Materials," Purdue University, Radiological and Environmental Management, printed: Jun. 21, 2017, pp. 1-3. https://www.purdue.edu/ehps/rem/hmm/pyro.htm.

"Guildelines for Handling Pyrophoric Materials," Environment Health and Safety Chemical Safety Update, University of California, San Francisco, printed: Jun. 21, 2017, pp. 1-5. http://ehs.ucsf.edu/sites/ehs.ucsf.edu/files/Guidehandlingpyrophorics 160222.1.pdf.

"Use a Syringe," How To page, Not Voodoo X, printed: Jun. 21, 2017, 1 page. http://chem.chem.rochester.edu/~nvd/pages/how-to.php?page=use_syringe.

"Luer taper," Wikipedia—The Free Encyclopedia, printed: Jun. 21, 2017, pp. 1-2. https://en.wikipedia.org/wiki/Luer_taper.

Errington, R.J., "3.4 Syringe and cannula techniques," Advanced Practical Inorganic and Metalorganic Chemisty, 1997, First edition, pp. 39-48, Blackie Academic & Professional. https://books.google.com/books?id=yl_mq_mCf2AC&pg=PA42&lpg=PA48#v=twopage&q&f=false.

* cited by examiner

SYRINGE ACCESSORY FOR TRANSFER OF AIR SENSITIVE MATERIALS

BACKGROUND

The present disclosure relates to syringe accessories and more specifically to syringe accessories for handling air sensitive materials.

An air sensitive fluid is any solution or pure liquid that reacts with common atmospheric components (e.g., water vapor, oxygen, carbon dioxide, pollutants, etc.). Examples of these reactions can include pyrolysis reactions, formation of metal oxides, hydrides, or sulfides, or formation of metal complexes with carbon dioxide molecules, etc. Air sensitive fluids are stored under an inert atmosphere (e.g., nitrogen or argon) in order to protect the fluids from reactive gases. For example, air sensitive fluids can be stored in ampules or in bottles with septum caps. Air sensitive fluids can also be stored in gloveboxes having inert atmospheres. A fluid can be transferred from the bottle by a syringe that pierces the septum.

SUMMARY

Various embodiments are directed to an apparatus for transferring fluid contained in a syringe. The apparatus can include an airlock component having a cylindrical body, the cylindrical body having a first end, a second end, and a hollow tube with an interior surface and an exterior surface disposed between the first end and the second end. The apparatus can also include an annular opening at the first end of the cylindrical body, as well as a gas inlet aperture from the exterior to the interior surface of the hollow tube, and a gas outlet aperture from the interior to the exterior surface of the hollow tube. The gas inlet aperture can have a hollow shaft extending outwardly, and the gas outlet aperture can include a one-way valve. Additionally, the apparatus can include an inwardly-facing airtight material (e.g., an O-ring or hollow plug), and a septum. The septum can be made from a material such as silicone or polytetrafluoroethylene (PTFE). Further, the apparatus can include an attachment member with a first end coupled to the second end of the cylindrical body, and a second end having elongate legs that form an annular body around an exterior surface of a container.

Additional embodiments are directed to a method of transferring a fluid. The method can include obtaining a fluid transfer apparatus having an attachment member coupled to an exterior surface of a container holding the fluid. The method can further include inserting a syringe coupled to a needle into an opening in the fluid transfer apparatus. Additionally, the method can include introducing an inert gas flow into the hollow tube, moving the syringe forward through the hollow tube toward the second end of the cylindrical body, puncturing the septum with the needle, and moving the syringe forward through the hollow tube so that the needle contacts the fluid in the container. The method can also include collecting a volume of liquid with the syringe, moving the syringe backward through the hollow tube until the needle is inside the hollow tube, and uncoupling the attachment member from the container. Additionally, the method can include coupling the attachment member to a second container, moving the syringe forward, puncturing the septum, and depositing the volume of liquid into the second container.

Further embodiments are directed to an article of manufacture that can include a syringe having a plunger, barrel, and tip coupled to a needle, and a fluid transfer apparatus. The needle can have a Luer lock hub. The fluid transfer apparatus can include an airlock component having a cylindrical body, the cylindrical body having a first end, a second end, and a hollow tube with an interior surface and an exterior surface disposed between the first end and the second end. The apparatus can also include an annular opening at the first end of the cylindrical body, as well as a gas inlet aperture from the exterior to the interior surface of the hollow tube, and a gas outlet aperture from the interior to the exterior surface of the hollow tube. The gas inlet aperture can have a hollow shaft extending outwardly, and the gas outlet aperture can include a one-way valve. Additionally, the apparatus can include an inwardly-facing airtight material (e.g., an O-ring) and a septum. The septum can be made from a material such as silicone or rubber. Further, the apparatus can include an attachment member.

DETAILED DESCRIPTION

Materials that are sensitive to gases found in ambient air are commonly used in laboratory and medical settings. These compounds are referred to as "air sensitive" compounds. "Ambient air" refers to the indoor or outdoor atmosphere (e.g., the Earth's atmosphere) in which the compounds are used or stored. The Earth's atmosphere and, thus, most ambient air is a mixture of approximately 78.09% nitrogen ($N_2$), 21.95% oxygen ($O_2$), 0.93% argon (Ar), 0.04% carbon dioxide ($CO_2$), 0.4-1% water vapor ($H_2O$), and small amounts (i.e., less than approximately 0.04%) of other gases (e.g., hydrogen ($H_2$), methane ($CH_4$), krypton (Kr), neon (Ne), helium (He), etc.) and pollutants (e.g., nitrogen dioxide ($NO_2$), sulfur dioxide ($SO_2$), ozone ($O_3$), carbon monoxide (CO), fine particles, acids, etc.). There are a wide variety of compounds that can react with at least one of these components. For example, metals (e.g., silver, iron, and copper) can become tarnished, rusted, or patinaed by gradual reactions with water, oxygen, and other atmospheric components. However, few compounds react with $N_2$ or the noble gases (Ar, He, Kr, and Ne). Therefore, these gases are referred to as "inert gases."

Materials that are referred to as air sensitive are typically those that react with oxygen and/or water vapor within a time scale short enough to require storage in an inert atmosphere (e.g., a time scale ranging from less than one second to several months). An inert atmosphere is an atmosphere of chemically unreactive gas or gases (e.g., an atmosphere substantially free of oxygen, water, carbon dioxide, etc.). Nitrogen ($N_2$) and argon (Ar) are the most commonly used inert gases in laboratory settings due to their relative abundance on Earth.

The nature of an air sensitive material's storage requirements primarily depends upon the speed of the reaction and the hazardousness of the material. Materials that react with oxygen and/or water vapor in less than a few months are often stored under an inert atmosphere in bottles with septum caps that can be pierced by an airtight syringe for safe removal and transfer. Some air sensitive materials react quickly (e.g., in seconds or minutes) and exothermically with components of ambient air, and can be dangerous. For example, pyrophoric materials spontaneously ignite in air at or below approximately 54.55° C. due to their reactivity with oxygen and/or water vapor. Examples of pyrophoric compounds that are commonly stored or transferred while dissolved in solution or as pure liquids can include metal hydrides, organolithium reagents, Grignard reagents, diphosphane, tert-butyllithium, trimethylaluminum, triethylborane, diethyl zinc, etc. Despite the dangers associated with pyrophoric compounds, many of these materials have wide applications in both commercial synthesis and research.

For example, tert-butyllithium (t-BuLi) is a commonly used strong base that can deprotonate compounds including amines and hydrocarbons. However, t-BuLi is an extremely pyrophoric liquid, and has caused numerous laboratory accidents and injuries. Therefore, t-BuLi must be stored in an airtight container under an inert atmosphere, and carefully transferred by airtight syringe or cannula. Additionally, working with t-BuLi in a laboratory glovebox or glovebag under an inert atmosphere can mitigate much of the danger, but this is not always practical. Further, even when t-BuLi is handled with proper air-free techniques, dangers can arise. A common problem with syringe or cannula transfer of t-BuLi is that a droplet of the liquid often remains on the tip of the needle during transfer, and this droplet can easily ignite. In addition to the danger caused by ignition of the droplet, one product of the pyrolysis reaction is a lithium salt, which can clog the needle when it precipitates.

An apparatus for airtight syringe transfer of air sensitive fluids is disclosed. The apparatus can be used with a syringe as an accessory for safe transfer of these fluids, or as a component of a device that includes a container or syringe. Herein, the term "airtight" is used to describe materials and seals that are substantially impermeable to gases and liquids. The fluid transfer apparatus encloses the needle of a syringe, along with part of the syringe barrel (i.e., the end of the barrel that is coupled to the needle), in a cavity filled with an inert gas as the syringe is used to withdraw a liquid from a container, transport the liquid, and inject the liquid into another container. Examples of containers can include bottles, vials, flasks, test tubes, etc. These containers have airtight septum caps (i.e., caps having membranes that are substantially impermeable to gases and liquids, but can be punctured by a needle). The septum caps prevent the liquids inside the containers from coming into contact with the ambient air. However, it should be noted that, in some embodiments, the containers do not have septum caps. This is discussed in greater detail below.

Figure 1:
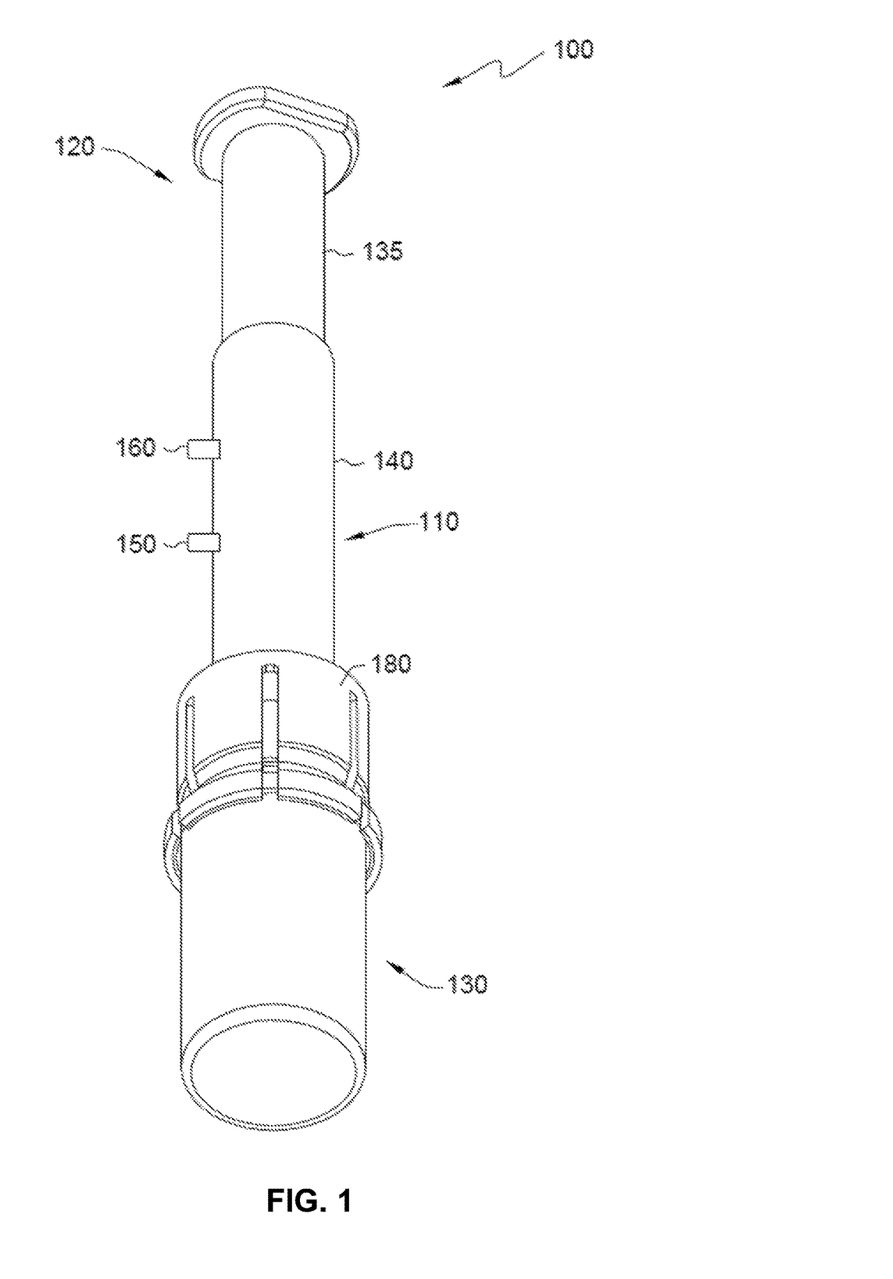
FIG. 1 is a schematic diagram illustrating a perspective view of a fluid transfer apparatus, syringe, and vial according to some embodiments of the present disclosure.

FIG. 1 is a schematic diagram illustrating a perspective view 100 of a fluid transfer apparatus 110, syringe 120, and vial 130 according to some embodiments of the present disclosure. The syringe includes a barrel 135. The syringe 120 also includes a plunger, and the syringe 120 is coupled to a needle. The needle and plunger are not illustrated in FIG. 1, and are discussed in greater detail below. The syringe 120 is a gas-tight syringe made from one or more materials such as glass, plastic, metal, etc. A gas-tight syringe is a type of syringe having a tight-fitting plunger that forms a seal with the interior wall of its syringe barrel, thereby preventing gases from entering or leaving the barrel at the end of the barrel opposite to the needle. However, it should be noted that syringes that are not gas-tight can be used in other embodiments. Additionally, a container other than a vial can be used (e.g., bottles, test tubes, flasks, etc.).

The fluid transfer apparatus 110 has an airlock component 140 with a cylindrical body in the shape of a hollow tube. However, it should be noted that the airlock component 140 can also have an elongate form that is polygonal (e.g., rectangular, triangular, hexagonal, etc.). In some embodiments, the airlock component 140 is plastic. However, the airlock component 140 can also be made of glass or metal. The airlock component 140 can be opaque or transparent, or it can be partly transparent and partly opaque. For example, an opaque tube could have a transparent window. Further, the airlock component 140 can include a gas sensor for determining the identity and concentration of gases inside of the hollow tube. This is discussed in greater detail with respect to FIG. 2.

Along the hollow tube of the airlock component 140 there is a gas inlet port 150 and a gas outlet port 160. The inlet port 150 is an aperture in the wall of the airlock component 140 from the exterior surface of the hollow tube to the interior surface of the hollow tube of the airlock component. The inlet port can have a hollow shaft that extends from the airlock component 140 surface perpendicularly or at an oblique angle. Airtight tubing connected to an inert gas source can be attached to the hollow shaft of the inlet port 150. Examples of airtight tubing can include rubber tubing, silicone tubing, latex tubing, and PTFE tubing. However, any other airtight tubing material can be used.

The gas outlet port 160 is an aperture in the wall of the airlock component 140 from the interior surface of the hollow tube to the exterior surface of the hollow tube of the airlock component. The gas outlet port 160 can include a one-way valve, or it can be a simple aperture with a hollow shaft extending from the outer surface of the airlock component, either perpendicularly or at an oblique angle. Further, the outlet port 160 can optionally be attached to tubing connected to a vacuum source in order to facilitate purging of the airlock component 140. Purging of the airlock component is discussed in greater detail with respect to FIG. 2. The hollow shafts of the inlet 150 and outlet ports 160 can optionally have annular serrations to aid in forming an airtight seal with the airtight tubing. It should be noted that, in some embodiments, the outlet port 160 does not have a shaft. Additionally, in some embodiments, the inlet port 150 connects directly to a gas source without the use of airtight tubing.

The airlock component 140 has a first end and a second end. The syringe 120 is inserted through the first end of the airlock component 140, and the second end of the airlock component 140 is coupled to a substantially annular opening at a first end of an attachment member 180. The attachment member 180 has a second end that engages with the vial 130. This is discussed in greater detail with respect to FIG. 2. In some embodiments, the first end of the attachment member 180 is coupled to the exterior surface of the airlock component 140 by friction. For example, if the circumference of the opening at the first end of the attachment member 180 is slightly larger than the circumference of the second end of the airlock component 140, the interior surface of the first end of the attachment member 180 can fit tightly around the exterior surface of the second end of the airlock component 140. In some embodiments, the attachment member 180 is plastic, though additional examples of attachment member 180 materials can include rubbers (e.g., natural rubber, butyl rubber, isoprene polymers, etc.), silicone, and metal. Attachment members are discussed in greater detail with respect to FIG. 3.

Figure 2:
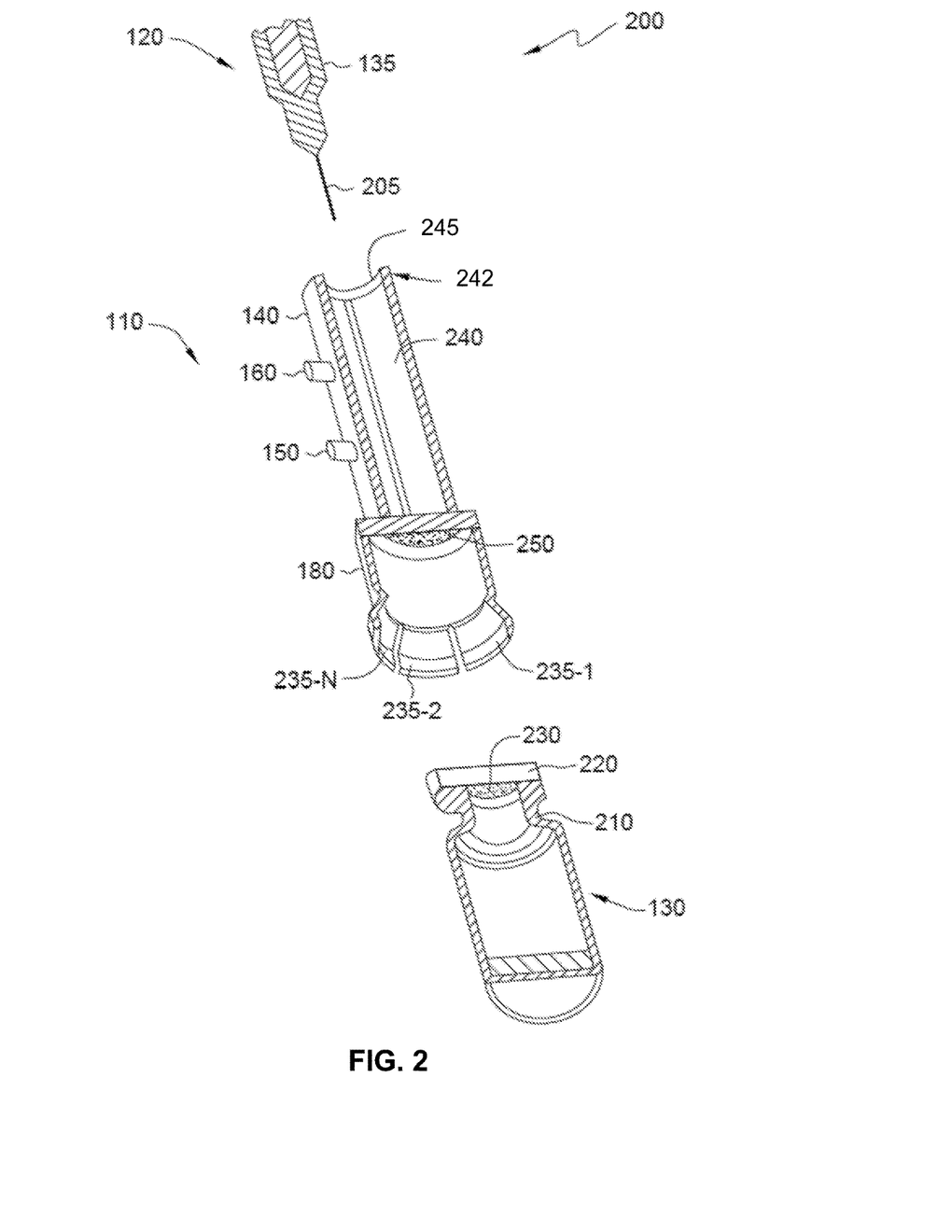
FIG. 2 is a schematic diagram illustrating a cross-sectional perspective view of the fluid transfer apparatus, the syringe, and the vial, according to some embodiments of the present disclosure.

FIG. 2 is a schematic diagram illustrating a cross-sectional perspective view 200 of the fluid transfer apparatus 110, the syringe 120, and the vial 130, according to some embodiments of the present disclosure. The barrel 135 of the syringe 120 tapers into a tip that is fitted to a hollow needle 205 for collecting fluid from the vial 130. The needle 205 can be coupled to the tip by a Luer lock hub or a slip hub, or the needle 205 can be non-releasably attached to the syringe 120. The vial 130 has a neck 210 coupled to a septum cap 220. The septum cap 220 can be part of a pre-attached airtight cap on a vial 130 containing liquid obtained from a commercial source, or the septum cap 220 can be placed on the vial 130 by a user. The septum cap 220 can be a plastic or metal cap (e.g., a screw cap or crown cap) with a substantially annular septum 230 made of a gas-impermeable material in the center of the cap 220. However, the septum cap 220 can also be a septum sleeve stopper. Examples of septum 230 materials can include silicone, rubbers (e.g., natural rubber, butyl rubber, isoprene polymers, etc.), polytetrafluoroethylene (PTFE), PTFE/silicone, PTFE/gray butyl, PTFE/rubber, silicone/aluminum, and fluoroelastomers. However, any other type of airtight septum can be used. In some embodiments, the vial 130 is a glass vial. However, the vial 130 can also be a plastic or metal vial.

The second end of the fluid transfer apparatus 110, which is connected to the attachment member 180, is coupled to the vial 130 by engaging the attachment member 180 with the neck 210 of the vial 130. The attachment member 180 extends from the airlock component 140, and engages with the outer surface of the vial neck 210. The attachment member 180 has elongate legs 235-1, 235-2, 235-N (referred to collectively as 235) that together form a substantially annular body surrounding the vial neck 210. In order to secure the fluid transfer apparatus 110 to the vial 130, the elongate legs 235 are extended in a radially outward direction around the neck 210 of the vial 130 when the neck 210 of the vial 130 is inserted between the legs 235. In some embodiments, an O-ring disposed on the interior surface of the attachment member 180 forms an airtight seal with the vial neck 210, though this O-ring is not illustrated herein.

The syringe 120 and needle 205 are inserted into an inner cavity 240 in the hollow tube of the airlock component 140 through a substantially annular opening 242 at the first end of the airlock component 140. The syringe 120 is inserted into the interior cavity 240 of the airlock component 140 so that the needle 205 and the barrel 135 of the syringe 120 enter through the annular opening 242. The annular opening 242 is coupled to an inwardly-facing O-ring 245 for making an airtight seal with the barrel 140 of the syringe 120 when the syringe 120 is inserted into the inner cavity 240. It should be noted that the position of the inwardly-facing O-ring 245 can vary longitudinally within the portion of the interior cavity 240 that is between the gas inlet 150 and outlet ports 160.

Further, the O-ring 245 can be replaced by another inwardly-facing material capable of forming an airtight seal with the barrel 135 of the syringe 120. For example, a hollow plug or disc made from an airtight material (e.g., rubbers, thermoplastics, silicone, PTFE, etc.) can be coupled to the interior surface of the airlock component 140 inner cavity 240. The syringe can be inserted through a hole or other opening in approximately the center of such a plug or disc. Different hole diameters could be used based on the diameter of the barrel of the syringe. Further, a hollow plug could extend outwardly from the first end of the airlock component 140.

Additionally, a seal between the substantially annular opening 242 and the syringe could be formed in the absence of an O-ring or plug by applying vacuum grease (e.g., hydrocarbon-based high vacuum grease, silicone grease, or Ramsay grease) between the surface of the syringe barrel 135 and the interior surface of the airlock component 140 at the first end. Further, it should be noted that, in some embodiments, an airtight seal can be made without an inwardly-facing airtight material. For example, a syringe barrel 135 that fits tightly into the annular opening, and makes contact with the interior surface of the airlock component 140, can prevent air from entering or leaving the interior cavity 240. In some embodiments, the syringe 120 could be non-releasably coupled to the airlock component 140, though able to move backward and forward within the interior cavity 240.

After the annular opening 242 at the first end of the airlock component 140 is sealed by the presence of the inserted syringe 120, the interior cavity 240 is purged in order to replace the ambient air inside of the cavity 240 with an inert gas. In purging the cavity 240, inert gas from a gas source (e.g., a gas tank or a Schlenk flask.) enters the cavity 240 through tubing fitted to the gas inlet port 150. As the inert gas enters through the inlet port 150, ambient air is forced out through the gas outlet port 160. Additionally, in some embodiments, the outlet port 160 is fitted to tubing connected to a vacuum source in order to facilitate removal of ambient air from the interior cavity 240.

Further, a gas sensor can be included in the airlock component 140. The gas sensor would allow a user to determine when purging is required by indicating the presence of gases that can react with the air sensitive compound to be transferred. Examples of gas sensors can include oxygen sensors (e.g., zirconia-based sensors, wideband zirconia-based sensors, titania-based sensors, Clark-type electrodes, and oxygen optodes), carbon dioxide sensors (e.g., nondispersive infrared (NDIR) $CO_2$ sensors, and chemical sensors based on polymer- or heteropolysiloxane), and water vapor sensors (e.g., colorimetric detectors, metal-coil type hygrometers, psychrometers, capacitive hygrometers, resistive hygrometers, thermal hygrometers, and gravimetric hygrometers).

A septum 250 is located at the second end of the airlock component 140. This septum 250 is referred to herein as the "airlock septum 250." The airlock septum 250 closes the second end of the airlock component 140 by covering the opening at the second end with an airtight seal. The airlock septum 250 prevents gases from entering or leaving the inner cavity 240 at the second end. Examples of gas-impermeable materials from which the airlock septum 250 can be made can include silicone, rubbers (e.g., natural rubber, butyl rubber, isoprene polymers, etc.), polytetrafluoroethylene (PTFE), PTFE/silicone, PTFE/gray butyl, PTFE/rubber, silicone/aluminum, PTFE/Thermoseal, and fluoroelastomers. However, any other type of airtight septum material can be used. The needle 205 of the syringe 120 is used to puncture the airlock septum 250. The syringe 120 is moved forward through the interior cavity 240, toward the second end of the airlock component 140. The syringe 120 is moved forward until the needle 205 punctures the airlock septum 250 and the vial septum 230, and comes into contact with fluid inside the vial 130. This is discussed in greater detail with respect to FIGS. 4 and 5.

Figure 3:
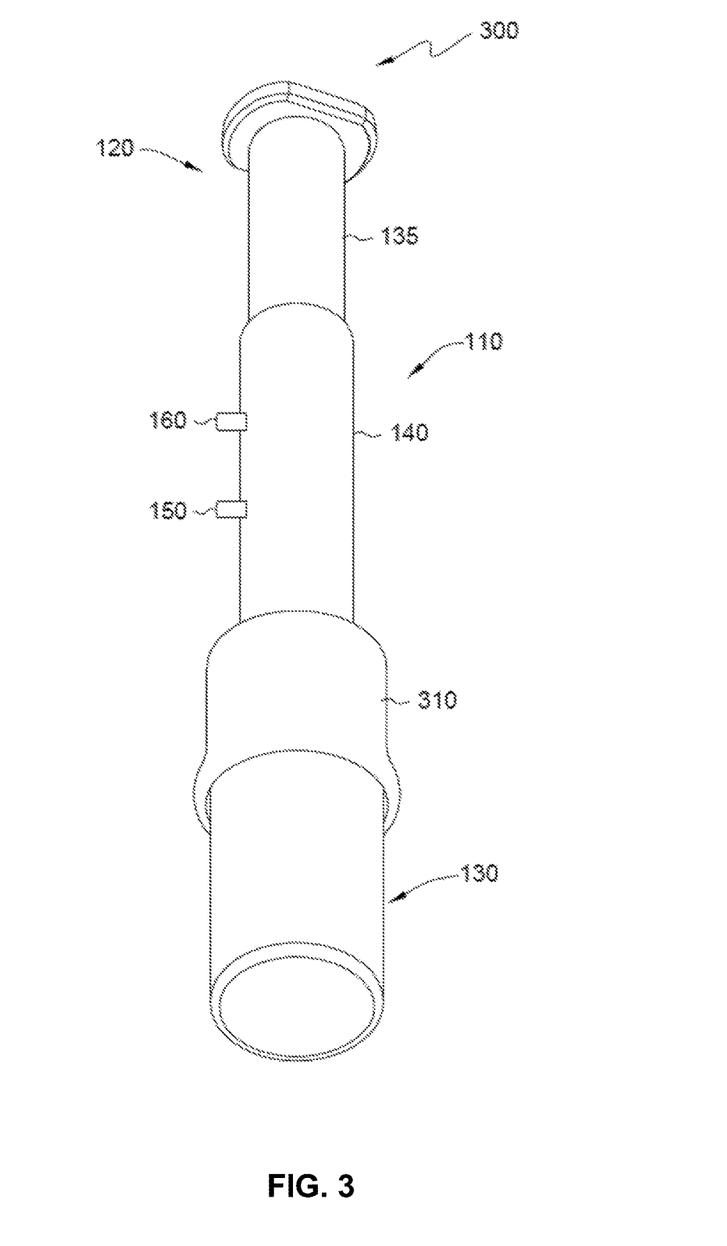
FIG. 3 is a schematic diagram illustrating a perspective view of the fluid transfer apparatus, wherein the fluid transfer apparatus has an alternative attachment member, according to some embodiments of the present disclosure.

FIG. 3 is a schematic diagram illustrating a perspective view 300 of the fluid transfer apparatus 110, wherein the fluid transfer apparatus has an alternative attachment member 310, according to some embodiments of the present disclosure. The alternative attachment member 310 on the fluid transfer apparatus 110 is made from a flexible material that is impermeable to gases and liquids (e.g., rubbers or silicone). This flexible attachment member 310 is pushed onto the vial 130 so that the attachment member 310 surrounds the neck of the vial 130. In some embodiments, the flexible attachment member 310 is flexible enough to be received by the vial 130, but resilient enough to form an airtight seal with the exterior of the vial 130.

It should be noted that other types of attachment members can be used in some embodiments. For example, attachment members can comprise Luer lock fittings, slip fittings, ground glass fittings, bayonet fittings, PTFE or plastic sleeves. The attachment member can be further secured to the vial neck by a joint clip (e.g., a Keck clip), and/or sealed with silicone grease or PTFE tape (e.g., Teflon tape). It should also be noted that, in some embodiments, the fluid transfer apparatus does not have an attachment member, and is instead secured with a clip, adaptor, tape, manually, etc. Further, the attachment member 180 or 310 can be non-releasably attached to the airlock component 140, or can be a part of the airlock component 140 itself. That is, the second end of the airlock component 140 could act as an attachment member in some embodiments.

Figure 4:
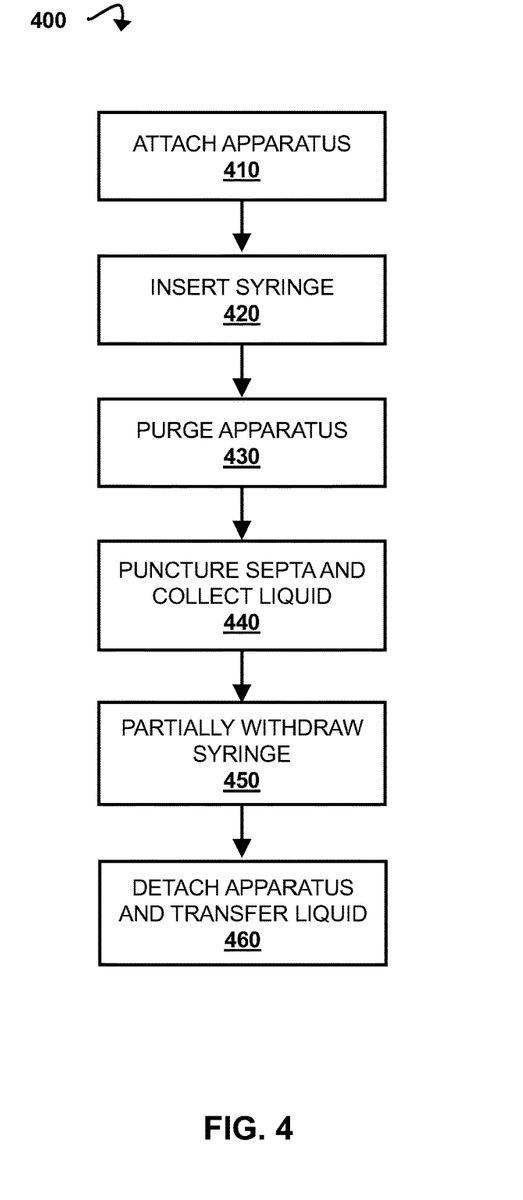
FIG. 4 is a flow diagram illustrating a process of transferring an air sensitive liquid using a fluid transfer apparatus, according to some embodiments of the present disclosure.

FIG. 4 is a flow diagram illustrating a process 400 of transferring an air sensitive liquid using a fluid transfer apparatus, syringe, and vial, according to some embodiments of the present disclosure. With reference to FIG. 4, the components of the fluid transfer apparatus, syringe, and vial can be the same as or substantially similar to the components of the fluid transfer apparatus 110, syringe 120, and vial 130 of FIGS. 1 and 2. The fluid transfer apparatus is coupled to a vial containing an air sensitive liquid. This is illustrated at step 410. The fluid transfer apparatus is coupled to the vial by engaging an attachment member with the neck of the vial, or by another attachment mechanism.

The syringe and needle are inserted into an annular opening at an end of the airlock component opposite to the attachment member. This is illustrated at step 420. The syringe is inserted so that the barrel of the syringe and the needle extend into the airlock component, but do not puncture the airlock septum. If the tube of the airlock component is made, at least in part, from a transparent material (e.g., glass or transparent plastic) the user can observe the position of the syringe within the interior cavity, thereby preventing inadvertent puncturing of the airlock septum. Additionally, a locking mechanism such as a metal or plastic clip can be releasably attached at the end of the airlock component coupled to the syringe in order to prevent the syringe from moving forward.

An appropriately sized syringe is chosen such that the barrel of the syringe forms an airtight seal with an inwardly-facing O-ring or other airtight material at the annular opening of the airlock component. Further, in some embodiments, the seal can be fortified by wrapping PTFE tape around the exterior of the first end of the airlock component and syringe barrel. Additionally, it should be noted that, in some embodiments, the syringe is inserted into the airlock component before the fluid transfer apparatus is coupled to the vial (i.e., steps 410 and 420 are reversed).

The airlock component is purged in order to replace the ambient air in its hollow interior with inert gas. This is illustrated at step 430. Purging with inert gas is done using standard air-free techniques, as would be understood by a person of ordinary skill in the art. An inlet port is connected to an inert gas source by airtight tubing. The gas flows into the hollow interior of the airlock component through an inlet port, and exits through an outlet port. Additionally, the syringe can optionally be purged by moving its plunger up and down at least once to expel the ambient air, and to introduce inert gas into the needle and barrel. The hollow interior of the airlock component is kept under positive pressure from the inert gas flow throughout the subsequent steps. In some embodiments, the airlock component has a gas flow or gas pressure sensor.

As inert gas flows through the interior cavity of the airlock component, the syringe is pushed forward until the needle punctures the airlock septum, and enters the vial, coming into contact with liquid in the vial. This is illustrated at step 440. In some embodiments, the needle punctures a septum in a septum cap on the vial. Additionally, the syringe can be filled with a volume of inert gas matching the volume of liquid to be withdrawn from the vial before the septa are punctured. However, the syringe can also contain a lower volume of inert gas, higher volume of inert gas, or no gas. The desired volume of liquid is collected by the syringe after any gas in the syringe is injected into the headspace. It should be noted that, in some embodiments, the vial or other liquid container does not have a septum cap. For example, a user could collect liquid from an open flask inside of a glovebox under an inert atmosphere, and use the fluid transfer apparatus and syringe to transfer the liquid to a second container outside of the glovebox.

Once the liquid has been collected, the needle is withdrawn from the vial. This is illustrated at step 450. The syringe is moved backward through the airlock component's hollow interior in order to withdraw the needle from the vial until the needle and part of the barrel of the syringe are inside the interior cavity of the airlock component. That is, the needle and syringe are returned to the position they were in at step 420. A locking mechanism, such as a plastic or metal clip, can optionally be disposed at the exterior of the annular opening and the syringe barrel in order to hold the syringe in place after it has been positioned. Further, a second locking mechanism could be coupled to the end of the syringe barrel that is opposite the tip in order to immobilize the plunger during transfer.

The fluid transfer apparatus and syringe are then detached from the neck of the vial, and transferred to another container. This is illustrated at step 460. The syringe and needle are not removed from the airlock component interior in this step. In some embodiments, the tubing is not removed from the fluid transfer apparatus before the transfer. However, the tubing may be removed, and the inlet and/or outlet ports can be covered or closed in order to maintain the inert gas atmosphere in the interior cavity of the airlock component. The fluid transfer apparatus holding the inert gas, the syringe containing air sensitive liquid, and the needle are then coupled to a second container by substantially the same methods as described with respect to step 410.

The syringe needle punctures the airlock septum, and the needle enters the second container by substantially the same methods as described with respect to step 440. In some embodiments, the second container has a septum cap. However, the second container can also be an open container under positive pressure from an inert gas, or an open container located in a glovebox under an inert atmosphere.

The liquid is deposited into the second container, and the needle is withdrawn from the container by substantially the same methods as described with respect to step 450.

Figure 5:
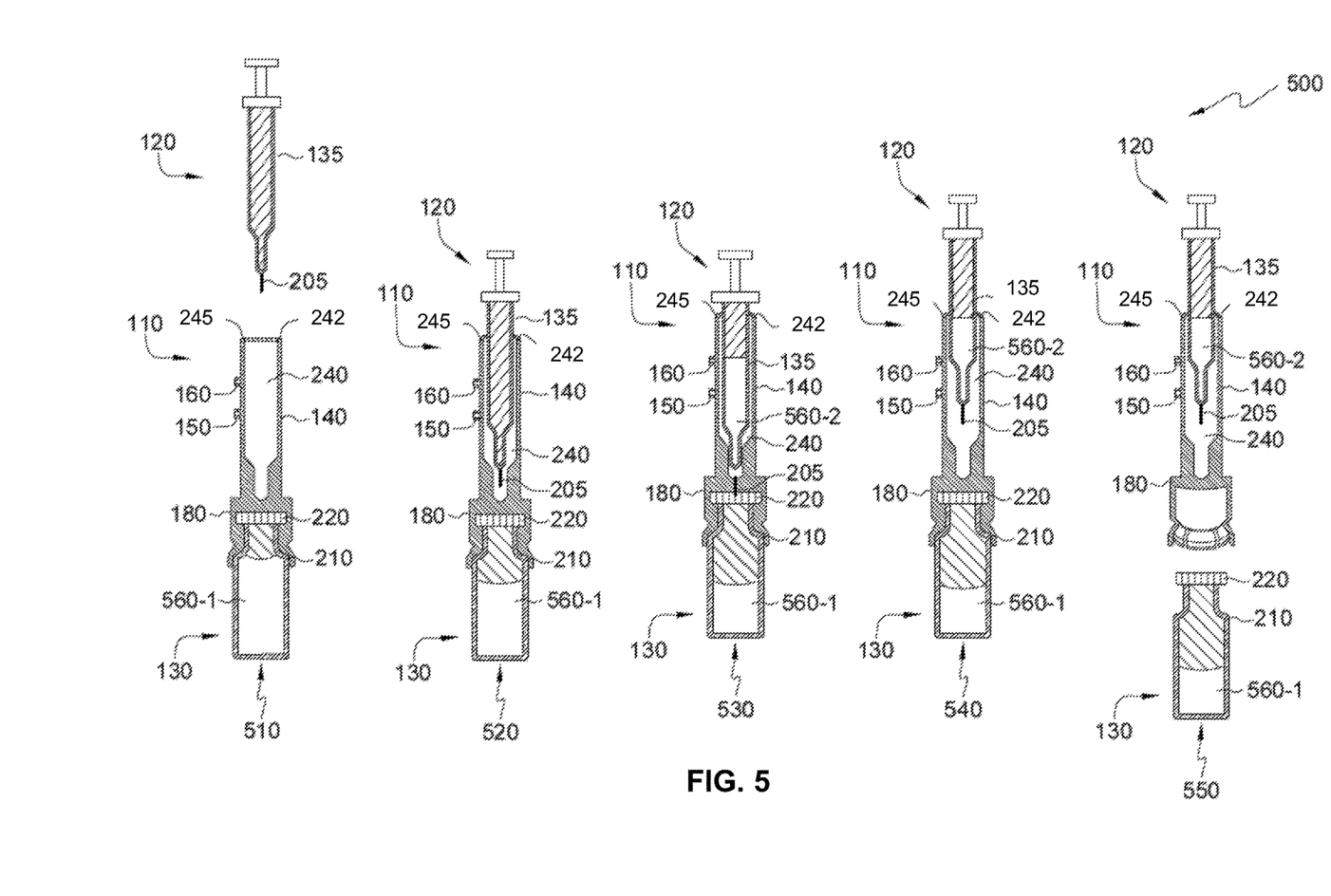
FIG. 5 is a series of schematic diagrams illustrating a visual process of transferring air sensitive liquid, according to some embodiments of the present disclosure.

FIG. 5 is a series 500 of schematic diagrams 510, 520, 530, 540, and 550 illustrating a visual process of transferring air sensitive liquid 560-1 and 560-2, according to some embodiments of the present disclosure. The visual process illustrated by these diagrams 500 is discussed with reference to process 400. Process 400 is described in greater detail with respect to FIG. 4. Diagram 510 is a visual representation of step 410. The fluid transfer apparatus 110 is coupled to the vial 130, which holds air sensitive liquid 560-1. The apparatus 110 is coupled to the vial 130 by engagement of the attachment member 180 with the neck 210 of the vial 130. The syringe 120 and needle 205 are not yet inserted into the airlock cavity 140.

Diagram 520 is a visual representation of steps 420 and 430 in process 400. In step 420, the empty syringe 120 and the needle 205 coupled to the syringe 120 are inserted into the interior cavity 240 of the fluid transfer apparatus 110. The syringe 120 and needle 205 are inserted through the annular opening 242 of the airlock cavity 140 so that the barrel 135 of the syringe 120 forms an airtight seal with the inwardly-facing O-ring 245 lining the annular opening 242. In step 430, the interior cavity 240 of the airlock component, the barrel of the syringe 120, and the needle 205 are purged with an inert gas that enters through the inlet port 150, and exits through the outlet port 160.

Diagram 530 is a visual representation of step 440 in process 400. In step 440, the syringe 120 is moved forward through the interior cavity 240 so that the needle 205 punctures the airlock septum 250 and vial septum 230. As the syringe 120 is moved forward, the barrel 135 maintains an airtight seal with the O-ring 245. Once the needle 205 has entered the vial 130, air sensitive liquid 560-1 in the vial is collected by the syringe 120. The liquid 560-2 inside of the syringe 120 is later transferred to another container.

Diagram 540 is a visual representation of step 450 in process 400. In step 450, the syringe 120, which contains the liquid 560-2 collected in step 440, is moved backward so that the needle 205 and part of the syringe barrel 135 are inside the interior cavity 240 of the airlock component. Diagram 550 is a visual representation of step 460 in process 400. In step 460, the fluid transfer apparatus 110, syringe 120, liquid 560-2, and needle 205 are disengaged from the vial 130 and transferred to at least one additional container. The additional container or containers are not illustrated in diagram 550.

In some embodiments, the fluid transfer apparatus 110 is used to transfer fluids that are not pyrophoric. Additionally, the fluid transfer apparatus 110 can be used to transfer fluids other than liquids (e.g., gases or plasmas). For example, the fluid transfer apparatus 110 can be used to transfer fluids that will react with components of small amounts of air entering the syringe through the needle in a non-pyrophoric manner. Examples of these fluids can include solutions of organometallic compounds with f-block or early d-block metals, hydrogen sulfide gas, nitric oxide gas, etc. Further, the fluid transfer apparatus can be used to transfer liquids that are dangerous if ingested, inhaled, and/or absorbed by the skin. This would prevent droplets of the dangerous liquids from coming into contact with a user, or with a surface that may be touched by a user. Examples of compounds such as these can include organomercury compounds, liquids containing viruses or bacteria, solutions containing cyanide ions, etc.

Further, the fluid transfer apparatus 110 can be a component of a fluid transfer and/or storage device, rather than an independent apparatus. In these instances, the fluid transfer apparatus component would be used in substantially the same way as the independent fluid transfer apparatus 110, despite being coupled to at least one additional component. For example, a fluid storage device could include a fluid transfer apparatus component non-releasably attached to a bottle or other container. Fluid could be removed from the fluid storage device with a syringe inserted through the airlock component into the bottle. Further, a fluid transfer device could include a fluid transfer apparatus component non-releasably attached to a syringe that is able to move backward and forward within the airlock component. The fluid transfer device would be coupled to a container holding an air sensitive liquid in the same manner as the fluid transfer apparatus 110.

The examples discussed herein and represented in the accompanying drawings may make reference to particular details. However, it will be understood that there are various modifications that can be made while retaining the spirit and scope of the disclosure. These would be easily recognized and carried out by one of ordinary skill in the art.

What is claimed is:

1. An apparatus for transferring fluid contained in a syringe, comprising:
   an airlock component having a cylindrical body, the cylindrical body having a first end, a second end, and a hollow tube disposed between the first end and the second end, wherein the hollow tube has an interior surface and an exterior surface;
   an annular opening at the first end of the cylindrical body;
   a gas inlet aperture from the exterior surface of the hollow tube to the interior surface of hollow tube;
   a gas outlet aperture from the interior surface of the hollow tube to the exterior surface of the hollow tube;
   an inwardly-facing airtight material coupled to the interior surface of the hollow tube; and
   a septum coupled to the second end of the cylindrical body.

2. The apparatus of claim 1, further comprising an attachment member having a first end coupled to the second end of the cylindrical body, and a second end having elongate legs that form an annular body around an exterior surface of a container.

3. The apparatus of claim 1, wherein the inwardly-facing material is an O-ring.

4. The apparatus of claim 1, wherein the inwardly-facing material is a hollow plug.

5. The apparatus of claim 1, wherein the septum is a silicone septum.

6. The apparatus of claim 1, wherein the septum is a PTFE septum.

7. The apparatus of claim 1, further comprising a hollow shaft extending outwardly from the gas inlet aperture.

8. The apparatus of claim 1, wherein the gas outlet aperture includes a one-way valve.

9. A method of transferring a fluid, comprising:
   obtaining a fluid transfer apparatus, the fluid transfer apparatus comprising:
      an airlock component having a cylindrical body, the cylindrical body having a first end, a second end, and a hollow tube disposed between the first end and the second end, wherein the hollow tube has an interior surface and an exterior surface;
      an annular opening at the first end of the cylindrical body;
      a gas inlet aperture from the exterior surface of the hollow tube to the interior surface of hollow tube;

a gas outlet aperture from the interior surface of the hollow tube to the exterior surface of the hollow tube;

an inwardly-facing airtight material coupled to the interior surface of the hollow tube;

a septum coupled to the second end of the cylindrical body; and an attachment member having a first end that is coupled to the second end of the cylindrical body;

coupling a second end of the attachment member to an exterior surface of a container holding the fluid;

inserting a syringe coupled to a needle through the annular opening at the first end of the cylindrical body;

introducing an inert gas flow into the hollow tube, wherein the inert gas flow enters the hollow tube through the gas inlet aperture, and exits the hollow tube through the gas outlet aperture;

moving the syringe forward through the hollow tube toward the second end of the cylindrical body;

puncturing the septum with the needle;

moving the syringe forward through the hollow tube so that the needle contacts the fluid in the container.

collecting, by the syringe, a volume of the fluid;

moving the syringe backward through the hollow tube until the needle is inside the hollow tube; and uncoupling the attachment member from the container.

10. The method of claim 9, further comprising:

coupling the attachment member to a second container;

moving the syringe forward through the hollow tube toward the second end of the cylindrical body;

puncturing the septum with the needle; and depositing the volume of the fluid into the second container.

11. The method of claim 9, wherein the container has a septum cap.

12. The method of claim 9, wherein the inwardly-facing airtight material is an O-ring.

13. The method of claim 9, wherein the inwardly-facing airtight material is silicone grease.

14. The method of claim 9, wherein the fluid is an air sensitive liquid.

15. An article of manufacture, comprising:

a syringe having a plunger, a barrel, and a tip;

a needle coupled to the tip of the syringe; and a fluid transfer apparatus, comprising:

an airlock component having a cylindrical body, the cylindrical body having a first end, a second end, and a hollow tube disposed between the first end and the second end, wherein the hollow tube has an interior surface and an exterior surface;

an annular opening at the first end of the cylindrical body;

a gas inlet aperture from the exterior surface of the hollow tube to the interior surface of hollow tube;

a gas outlet aperture from the interior surface of the hollow tube to the exterior surface of the hollow tube;

an inwardly-facing airtight material coupled to the interior surface of the hollow tube; and a septum coupled to the second end of the cylindrical body.

16. The article of manufacture of claim 15, further comprising an attachment member having a first end coupled to the second end of the cylindrical body, and a second end having elongate legs that form an annular body around an exterior surface of a container.

17. The article of manufacture of claim 15, wherein the needle has a Luer lock hub.

18. The article of manufacture of claim 15, wherein the inwardly-facing airtight material is an O-ring.

19. The article of manufacture of claim 15, wherein the septum is a silicone septum.

20. The article of manufacture of claim 15, wherein the septum is a rubber septum.

* * * * *